United States Patent [19]

Margolin

[11] Patent Number: 5,310,562
[45] Date of Patent: May 10, 1994

[54] COMPOSITION AND METHOD FOR REPARATION AND PREVENTION OF FIBROTIC LESIONS

[76] Inventor: Solomon B. Margolin, 6723 Desco Dr., Dallas, Tex. 75225

[21] Appl. No.: 947,995

[22] Filed: Sep. 21, 1992

Related U.S. Application Data

[63] Continuation of Ser. No. 737,914, Jul. 26, 1992, abandoned, which is a continuation-in-part of Ser. No. 440,978, Nov. 22, 1989, abandoned.

[51] Int. Cl.$^5$ .......... A61K 9/02; A61K 9/14; A61K 9/20; A61K 9/48
[52] U.S. Cl. .......... 424/489; 424/423; 424/427; 424/436; 424/451; 424/464; 514/838; 514/824; 514/851; 514/866
[58] Field of Search .......... 424/435, 423, 427, 436, 424/451, 461, 489; 514/851, 838, 824, 866

[56] References Cited

U.S. PATENT DOCUMENTS

| | | | |
|---|---|---|---|
| 3,839,346 | 10/1974 | Gadekar | 514/821 |
| 3,974,281 | 8/1976 | Gadekar | 514/345 |
| 4,042,699 | 8/1977 | Gadekar | 514/345 |
| 4,052,509 | 10/1977 | Gadekar | 514/345 |

OTHER PUBLICATIONS

Abstract No. 7480, Federation Proceedings, vol. 41, No. 6, Mar. 10, 1982, Federation of American Societies for Experimental Biology.

*Primary Examiner*—Thurman K. Page
*Assistant Examiner*—James M. Spear
*Attorney, Agent, or Firm*—John H. Crozier

[57] ABSTRACT

In a preferred embodiment, drugs having heretofore unknown pharmacological properties which are useful in the medicinal therapy of fibrotic disease for the reparation and prevention of fibrotic lesional tissues, such drugs including as the active ingredient 5-methyl-1-phenyl-2-(1H)-pyridone. The pharmaceutical composition of this invention is novel as an anti-fibrotic drug, namely, as an agent for treating fibrosis. Any existing compounds have not been shown to be effective for the reparation and prevention of fibrotic lesions.

18 Claims, 1 Drawing Sheet

FIG. 1

COMPOSITION AND METHOD FOR REPARATION AND PREVENTION OF FIBROTIC LESIONS

This is a continuation of co-pending application Ser. No. 07/737,914, filed on Jul. 26, 1992, now abandoned, which is a continuation-in-part of co-pending application Ser. No. 07/440,978, filed on Nov. 22, 1989, now abandoned.

BACKGROUND OF THE INVENTION

1. Field of the Invention

The present invention relates to a medical composition for the reparation of fibrotic lesional tissues and the prevention of fibrotic lesions, which composition comprises 5-methyl-1-phenyl-2-(1H)-pyridone as an active anti-fibrotic ingredient.

2. Background Art

Herein, the term "anti-fibro", "anti-fibrotic" or "anti-fibrosis" refers to prevention of pathological polymerization of collagen in lung fibrosis, arteriosclerosis, prostatic hypertrophy, keloid, myocarditis, collagen disease, scar, wrinkle, etc., and reparation as well normalization of the existing pathological fibrotic tissues.

5-Methyl-1-phenyl-2-(1H)-pyridone itself is a known compound and its pharmacological effects are disclosed, for example, in Japanese Patent Application KOKAI (Laid-Open) Nos. 87677/1974 and 1284338/1976 as an anti-inflammatory agent including antipyretic and analgesic effects. U.S. Pat. Nos. 3,839,346, issued Oct. 1, 1974; U.S. Pat. No. 3,974,281, issued Aug. 10, 1976; U.S. Pat. No. 4,042,699, issued Aug. 16, 1977; and U.S. Pat. No. 4,052,509, issued Oct. 4, 1977, also describe methods of manufacture of 5-methyl-1-phenyl-2-(1H)-pyridone and its use as an anti-inflammatory agent and the disclosures of those patents are incorporated herein by reference.

It has been discovered by the present inventor that the compound has an anti-fibrotic activity. Heretofore, no effective pharmacological agent or composition has been available for the prevention or removal of pathologic fibrotic lesions of the lungs, prostate glands, musculoskeletal diseases, myocardial degeneration, myocardial infarction, arteriosclerosis, and other lesional fibroses.

For example, powerful anti-inflammatory glucocorticoids (hormones relating to carbohydrate metabolism) such as hydrocortisone or prednisolone administered in very large doses have repeatedly been shown to be ineffective against fibrotic disease. These glucocorticoids do not arrest or remove such life-threatening fibrotic lesions. The glucocorticoids may be effective, however, as anti-inflammatory agents under such condition that they may temporarily ameliorate the secondary acute inflammation flare-ups which intermittently occur in tissues or organs damaged by fibrotic disease. Indeed, excessive and prolonged administration of glucocorticoids in pulmonary fibrotic disease may cause destruction of tissues, due to fibrosis or an exacerbation and acceleration of the fibrotic destruction.

Antopol (1950) was the first of many investigators who found that the anti-inflammatory glucocorticoids readily enhance fibrotic degeneration of lung tissues. Similarly, the non-steroidal anti-inflammatory agents such as aspirin, salicylates, phenylbutazone, indomethacin, various phenylacetic acid derivatives, and the like have also failed to arrest formation of, or cause repair of progressive, chronic fibrotic damage to lung tissues, prostatic tissues, musculoskeletal tissues, etc.

Accordingly, it is a principal object of the present invention to provide compositions for the reparation and prevention of fibrotic lesional tissue.

It is an additional object of the invention to provide such compositions that comprise 5-methyl-1-phenyl-2-(1H)-pyridone as an active anti-fibrotic ingredient.

Other objects of the present invention, as well as particular features and advantages thereof, will be elucidated in, or be apparent from, the following description and the accompanying drawing figure.

SUMMARY OF THE INVENTION

The present invention overcomes the limitations of the prior art by providing, in a preferred embodiment, drugs having heretofore unknown pharmacological properties which are useful in the medicinal therapy of fibrotic disease for the reparation and prevention of fibrotic lesional tissues, such drugs including as the active ingredient 5-methyl-1-phenyl-2-(1H)-pyridone. The composition of this invention is novel as an anti-fibrotic drug, namely, as an agent for treating fibrosis. Any existing compounds have not been shown to be effective for the reparation and prevention of fibrotic lesions. The active ingredient exerts an anti-fibrotic activity quite dissimilar to and independent of fibrinolytic activity.

DETAILED DESCRIPTION OF THE PREFERRED EMBODIMENTS

The "anti-fibrotic" activity described herein differs from "fibrinolytic" or "anti-fibrin" activity. The "fibrinolytic" or "anti-fibrin" activity refers to the biological ability of a pharmaceutical substance to (1) prevent fibrin formation (prevent formation of a blood clot) or (2) lyse or dissolve a previously formed blood clot.

The "anti-fibrotic" activity discovered by the present inventor and as used herein refers to the ability of an active substance to (1) prevent an excessive pathologic accumulation of collagenous scar or connective tissue in various body structures and organs (usually triggered by some injury, allergy, infection, or by some inherited genetic aberration), or (2) cause the non-surgical removal or biological dissolution of an existing excessive and pathologic accumulation of fibrotic collagenous tissue (for example, as in the dissolution of life-threatening fibrotic lesions of the lung found in patients with asbestosis).

A. Connective Tissue Proteins of Mammals

Three major classifications of connective tissue proteins are recognized with the largest portions consisting of collagen types (70 to 80%) and elastin types (15 to 20%). A miscellaneous group constitutes the third and smallest class.

The general biochemical characteristics of the collagen types which constitute the principal protein (1) in normal white connective tissue and (2) in scar or fibrotic tissue, are summarized in Table 1, as contrasted with elastin types. For example, collagen is sparingly soluble in water, but readily converted to water soluble gelatin upon boiling in an acid or alkali. In contrast, the highly water soluble elastin does not convert to gelatin upon boiling in an acid or alkali.

The elastin constitutes the principal protein of yellow connective tissue found in elastic structures such as the walls of larger blood vessels and walls of lung alveoli.

Investigations on the molecular biochemical level of tissues have demonstrated a very slow turnover rate for metabolic processes involving fibrotic lung collagen. In fact, the metabolic rate is measured in years. By contrast, the metabolic rates of the other connective tissue collagens including elastin and the like are measured and expressed in hours and days (White, Handler, and Smith, 1973, page 983).

B. Interstitial Proliferation (Hyperplasia) of Fibroblast-Type Cells in Lungs and Other Organ Tissues The synthesis of various collagens found in scar or fibrotic structures takes place in fibroblast cells which then extrude the collagen into the surrounding matrix. During this wound repair process, there are (1) a rapid proliferation and increase in the number of fibroblasts at the site, and (2) a sharp rise in the rate of the synthesis and extrusion of collagen. If these two phenomena are not prevented, the pathologic and progressive accumulation of collagen would cause polymerization and fibrotic disease (for example, impairment of respiratory function, impaired circulatory function via fibrotic changes in arterial walls, fibrotic degeneration of renal and liver function, degenerative musculoskeletal function, fibrotic degeneration of cardiac muscle or skeletal muscle, fibrotic degenerative changes in neuronal tissues in the central nervous system as well as the peripheral nervous system, etc.). [S. L. Robbins, R. S. Cotrans, V. Kumar, "Pathologic Basis of Disease", 6th edition, pages 40–84, Saunders, Philadelphia, Pa. (Pub.)].

With pulmonary interstitial fibrotic hyperplasia, small and firm nodules are palpable throughout the lung tissue, and upon gross examination are recognized from their opaque, airless structure to be foci of abnormal accumulations of fibrotic connective tissue. Such foci vary in size and color according to their age. Their aggressive and continued enlargement and coalescence ultimately leads to collagenous solidification of large segments of the lungs.

These enlarging foci also impinge upon the lung capillaries thereby to reduce pulmonary blood flow, and at the same time, impede lymphatic drainage from the lungs. As a consequence, exudate accumulates within the alveoli, and secondary thickening of the alveolar wall ensues. These interacting processes sharply reduce the efficiency of the gaseous exchange in the lung alveoli, which is a primary function of the normal lung.

In addition, these pulmonary fibrotic alternations and accumulations raise the pulmonary blood vessel resistance and lead to cor pulmonale (sharply elevated pulmonary blood pressure). Prolonged elevated pulmonary blood pressure almost invariably leads to congestive heart failure in addition to the cyanosis caused by inadequate pulmonary exchange of oxygen and carbon dioxide. The prognosis is poor and the incidence of severe morbidity and deaths is high.

Furthermore, the fibrosis of the lung impairs the physiological and biochemical functions of the lung that are independent of the pulmonary gas exchange (oxygen and carbon dioxide) role of the lungs cited above. These Include:

(1) filtration, degradation, and removal of the following substances:
  (a) aged leucocytes from the blood, and
  (b) particulate matter (for example, tissue cell debris, blood cell aggregates, inert foreign matter, small thrombi); and
(2) synthesis of adequate supplies of heparin.

Heparin is a useful substance that normally prevents the formation of life-threatening blood clots in the major blood vessels (for example, cerebral and coronary blood vessels).

C. Differentiation Between Anti-Fibrotic Activity and Anti-Inflammatory Activity Pharmacological anti-fibrotic activity as exemplified by the arrest and removal of lung scarring (interstitial hyperplasia and fibrotic foci), or pathologic fibrotic lesions in other organs and tissues described herein, is clearly distinct from and independent of any pharmacological anti-inflammatory activity.

The debilitating pathologic degeneration of organs and tissues affected by fibrotic disease continues for extended periods of time, measured in months or years, beyond the short-term (hours and days) of exacerbating inflammatory flare-ups (classical clinical and histopathological signs of edema, local heat, and leucocytic infiltration have disappeared).

The composition of this invention is effective for treatment of disease caused by the pathologic and excessive fibrotic accumulations such as pulmonary fibrosis, benign prostate hypertrophy, coronary infarcts, cerebral infarcts, myocardiac fibrosis, musculoskeletal fibrosis, post-surgical adhesions, liver cirrhosis, real fibrotic disease, fibrotic vascular disease (atherosclereosis, varix, or varicose veins), scleroderma, Alzheimer's disease, diabetic retinopathy, glaucoma, etc. The pulmonary fibrosis may have been chemically induced, for example, by the anti-cancer drugs bleomycin or cyclophosphamide or by the weed killer paraquat. 5-Methyl-1-phenyl-2-(1H)-pyridone (5MP2P) not only arrests the formation of new fibrotic tissue but causes removal of previously formed fibrotic collagen-containing tissue. These pharmacological properties of 5MP2P are heretofore unknown.

This has been repeatedly demonstrated in experimentally induced pulmonary fibrosis, and in humans with advanced life-threatening pulmonary fibrosis.

The present invention described a method for arresting formation of or causing removal of a pathogenic accumulation of water-insoluble collagenous connective tissue (for example, excessive scar or lesional fibrotic tissue, etc.). By medicinally removing such pathologic collageneous tissue in fibrotic lungs, 5MP2P eliminates or prevents:

(1) the mechanical compression or occlusion (stenosis) of blood vessels (for example, pulmonary arteries, veins, and capillaries), pulmonary bronchioles, and alveoli;
(2) the inhibition of the primary respiratory function of the alveoli of the lungs, namely, the exchange of oxygen and carbon dioxide gases; and
(3) the increased pulmonary blood vessel resistance (cor pulmonale) which readily causes fatal congestive heart failure because of the excessive workload on cardiac muscle that is engendered by the cor pulmonale.

The dramatic and novel pulmonary anti-fibrotic activity by 5MP2P has been observed and demonstrated in laboratory animal experiments (rats, hamsters, dogs) and in humans. The anti-fibrotic activity in cardiac infarctions, benign prostatic hypertrophy, and post-operative adhesions has been observed in humans. The renal anti-fibrotic activity has been demonstrated in hamsters. In every instance, the anti-fibrotic activity was clearly distinct from any anti-inflammatory properties.

The acute toxicity of the ingredient in the medical composition of the present invention which exerts the anti-fibrotic activity is as shown in the table below:

| | ACUTE TOXICITY ($LD_{50}$:mg/kg) | | | |
|---|---|---|---|---|
| | Route for Administration | | | |
| Animal | p.o. (number) | i.v. (number) | i.p. (number) | 10% Ointment p.o. (number) |
| Mouse: | 997.7(40) | 285 ± 5(50) | 600 ± 43(60) | 11,500 + 1,100(43) |
| Rat: | | | | |
| Male: | 1,295(25) | | 430 ± 29(42) | 12,500(10) |
| Female: | 2,300(30) | | | |
| Guinea Pig: | 810 ± 25(30) | | 460 + 28(25) | |
| Rabbit: | | 280 ± 32(12) | | |
| Cat: | 500(17) | 40(4) | | |
| Dog: | 300(11) | 200(6) | | |
| Monkey: | | 100(3) | | |

Hereafter the present invention is described by referring to examples below.

The anti-fibrotic activity measured against pulmonary fibrosis was found to be quite dissimilar to and independent of anti-flammatory activity when these activities were assayed in rats and hamsters. Experiments in dog and human clinical trials affirm these findings. 5MP2P has been extensively studied for oral anti-fibrotic activity in laboratory animals and in humans. The anti-fibrotic effect in pulmonary fibrosis was demonstrated upon oral administration:

(1) in diets or by gavage to rat or hamsters,
(2) oral capsules in dogs, and
(3) oral administration to humans.

EXAMPLE 1

The results of a histopathological examination of the lungs of rats for fibrosis (interstitial hyperplasia) after receiving 300 mg/kg body weight of 5MP2P in the diet for three months are summarized in Table 2. The individual microscopic readings of the lung are also shown in Table 2, where a score schedule of 0, 1, 2, and 3 reflects the degree of fibrosis.

The data in Table 2 reveal a statistically significant reduction in the amount of fibrosis in rats receiving 5MP2P as compared to placebo control rats (Group 1). The mean score for the controls (Group 1) was 1.63+0.23, and for Group IV (5MP2P, 300 mg/kg body weight daily was 0.95+0.23.

Student's T value was 2.43, with P less than 0.02 (highly significant statistically).

Figure 1:
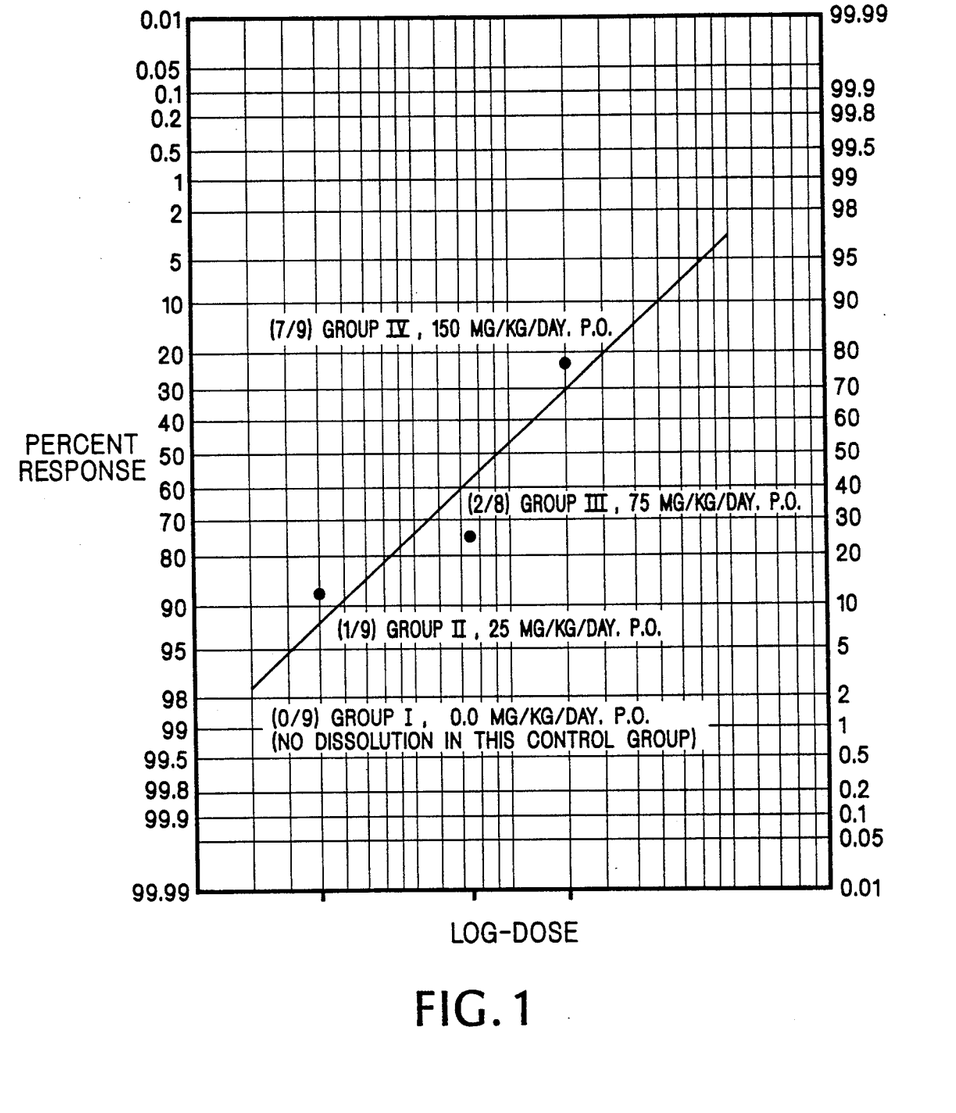
FIG. 1 is a graph representing data of animal tests shown in Table 3, indicating the effect of the drug of the present invention.

In male and female Beagle dogs, the anti-fibrotic activity was found to be a direct function of the dosage of 5MP2P administered, a classical pharmacological dose-response (Table 3, FIG. 1). Lung tissues examined microscopically, and scored on a schedule of 0, 1, 2, and 3 for fibrosis resulted in clear demonstration of statistically significant reduction in pulmonary fibrosis in dogs given the drug as compared to control animals.

The mean score for Group I (Control) was 2.11±0.31, and for Group IV, which received 5MP2P, 150 mg/kg per day orally in capsules, was 0.22±0.15.

In hamsters, pulmonary fibrosis induced with cryosotile asbestos was removed following oral 5MP2P (Table 4).

This anti-fibrotic activity was not simply a palliative (relieving) effect.

The asbestos-induced fibrosis did not recur after the 5MP2P had been discontinued for two months. In mice, pulmonary fibrosis induced with cyclophosphamide was removed following oral administration of 5MP2P (Table 5). Cyclophosphamide is an anti-cancer agent and an immunosuppresant drug in humans and is known to produce pulmonary fibrosis in patients as a side effect.

A similar experience has been observed in trials on human patients with pulmonary fibrosis caused by asbestos.

For the first time ever, 5MP2P makes possible a pulmonary resolution process whereby a life-threatening solidified fibrotic lung disease can be restored to a relatively normal tissue where the alveoli are no longer collapsed or occluded. That is, the microscopic examination reveals that the tissues are regenerated and become normal, spongy lungs.

The novel role of 5MP2P in the therapeutic repair of fibrotic lung tissue featuring removal of fibrotic lesions, and concomitant regeneration of normal lung tissue has been observed in experimental asbestosis by histopathological examination of lung tissue specimens under the light microscope, and electron microscopy (Table 4).

Very little, if any, fibrotic alterations are seen after treatment with adequate doses of 5MP2P.

A further novel discovery was the demonstration under the electron microscope that the lung cell-imbedded asbestos fibers which had initiated and maintained the extensive fibrotic lesions also had been removed. This was subsequently confirmed by ashing of lung specimens in a laboratory oven, and then determining the asbestos content.

The discovery of this additional novel "clearing" property of 5MP2P for the first time affords a therapeutic pharmacological remedy for chronic respiratory disease caused by the inhalation and accumulation in the lungs of harmful foreign matter from polluted air, asbestos, industrial dust (grain, lime, fertilizers, cotton fibers, glass fibers, plastics, coal, etc.), resulting in asbestosis, silicosis, and/or black lung of miners, for example.

TABLE 1

CONTRAST BETWEEN PROPERTIES OF COLLAGEN AND ELASTIN

| Property | Collagen | Elastin |
|---|---|---|
| 1. Water soluble | − | + |
| 2. Converts to gelatin on boiling | + | − |
| 3. Primarily in white connective tissue | + | − |
| 4. Primarily in yellow connective tissue | − | + |
| 5. Primarily associated with highly elastic structure (e.g., blood vessels) | − | + |
| 6. Primarily in organ structural tissue; fibrotic or scar tissue (e.g., lung fibrosis, etc.) | + | − |
| 7. Metabolic turnover rate | low | high |

TABLE 2

| Animal Number | Sex | Lung Connective Tissue Score | | | |
|---|---|---|---|---|---|
| | | 0 | 1 | 2 | 3 |
| GROUP I (CONTROL) | | | | | |
| 104 | F | | | | x |
| 8 | M | | | x | |
| 72 | F | x | | | |
| 74 | F | | | | x |
| 75 | F | | x | | |
| 80 | F | | | x | |
| 81 | F | | | x | |
| 82 | F | | x | | |
| 88 | F | | | x | |
| 94 | F | | x | | |
| 1 | M | | x | | |
| 19 | M | | x | | |
| 26 | M | | x | | |
| 36 | M | | x | | |
| 43 | M | | | | x |
| 45 | M | x | | | |
| 52 | M | | x | | |
| 53 | M | | | x | |
| 55 | M | | x | | |
| Total: | | 2 | 8 | 4 | 5 |
| Mean: 1.63 | | | | | |
| S.E. 0.23 | | | | | |
| GROUP IV: 5MP2P, 300 mg/kg (p.o.) | | | | | |
| 95 | F | | x | | |
| 86 | F | | | | x |
| 93 | F | | x | | |
| 97 | F | x | | | |
| 98 | F | | x | | |
| 99 | F | | x | | |
| 119 | F | | x | | |
| 122 | F | | x | | |
| 123 | F | x | | | |
| 135 | F | x | | | |
| 5 | M | | x | | |
| 11 | M | | x | | |
| 16 | M | | x | | |
| 29 | M | x | | | |
| 31 | M | x | | | |
| 32 | M | | x | | |
| 34 | M | | x | | |
| 35 | M | | | x | |
| 40 | M | | | x | |
| Total: | | 5 | 11 | 2 | 1 |
| Mean: 0.95 | | | | | |
| S.E.: 0.18 | | | | | |
| t: 2.43 | | | | | |
| P: <0.02 | | | | | |

TABLE 3

EFFECT OF ORAL 5MP2P UPON PULMONARY INTERSTITIAL HYPERPLASIA (FIBROSIS) IN DOGS

| Group | Number of Dogs | Hyperplasia Scores* | | | | Average Scores | Incidence of Normal Lung |
|---|---|---|---|---|---|---|---|
| | | 0 | 1 | 2 | 3 | | |
| I. Control (0.0%) | 9 | 0 | 3 | 2 | 4 | 2.11 ± 0.31 | 0/9 |
| II. 5MP2P (16.7%) 25 mg/kg/day | 6 | 1 | 1 | 4 | 0 | 1.50 ± 0.34 | 1/6 |
| III. 5MP2P (25.0%) 75 mg/kg/day | 8 | 2 | 2 | 3 | 1 | 1.38 ± 0.38 | 2/8 |
| IV. 5MP2P 150 mg/kg/day | 9 | 7 | 2 | 0 | 0 | 0.22 ± 0.15** | 7/9 |

*Degree of Hyperplasia (fibrosis)
0 = normal tissue
1 = minimal
2 = moderate
3 = severe
**Highly Statistically Significant (P < 0.001)

TABLE 4

EFFECT OF ORAL 5MP2P UPON ASBESTOS-INDUCED PULMONARY INTERSTITIAL FIBROSIS IN HAMSTERS

| Group | Animal Number | Lung Density | Pulmonary Fibrosis Score | |
|---|---|---|---|---|
| | | | Light Microscope | Electron Microscope |
| I. Control | 1 | 0.95 | 0 | 0 |
| No Asbestos (−); | 2 | 0.90 | 1 | 0 |
| No 5MP2P | 3 | 1.05 | 1 | 1 |
| | 4 | 1.10 | 0 | 0 |
| Average | | 1.00 ± 0.05 | 0.50 ± 0.25 | 0.25 ± 0.25 |
| II. Asbestos (+); | 5 | 2.70 | 3 | 3 |
| No 5MP2P (−) | 6 | 1.90 | 2 | 3 |
| | 7 | 2.53 | 3 | 2 |

TABLE 4-continued

EFFECT OF ORAL 5MP2P UPON ASBESTOS-INDUCED
PULMONARY INTERSTITIAL FIBROSIS IN HAMSTERS

| Group | Animal Number | Lung Density | Pulmonary Fibrosis Score Light Microscope | Pulmonary Fibrosis Score Electron Microscope |
|---|---|---|---|---|
| | 9 | 2.98 | 3 | 3 |
| Average | | 2.53 ± 0.23 | 2.75 ± 0.25 | 2.75 ± 0.25 |
| III. Asbestos (+)*: | 10 | 0.98 | 0 | 0 |
| Plus 5MP2P (+) | 12 | 1.04 | 2 | 1 |
| | 13 | 1.26 | 1 | 0 |
| | 14 | 1.41 | 1 | 0 |
| Average | | 1.17 ± 0.10 | 1.00 ± .41 | 0.25 ± 0.25 |
| Student's "T" Values: | | | | |
| Group II vs. Group III: | | 5.9** | 3.7** | 7.1** |
| Group II vs. Group I: | | 6.5** | 5.9** | 7.1** |

Degree of Fibrosis:
0 = normal tissue
1 = minimal
2 = moderate
3 = severe

*Asbestos by inhalation for 5 days; 5MP2P, 500 mg/kg/day, orally in the diet for two months, beginning two months after the five-day exposure to asbestos dust.
**Statistically Significant ($P < 0.001$)

TABLE 5

Clinical human open trials have been undertaken as follows:

1. Pulmonary fibrosis diagnosed as caused by asbestos was treated with 5MP2P and closely and objectively followed in two subjects. Clinical impressions were dramatic and highly favorable.
2. Pulmonary fibrosis diagnosed as idiopathic in nature was treated with 5MP2P and closely and objectively followed in one subject for over two years. Clinical impressions were highly favorable.
3. Benign prostate hypertrophy in three elderly subjects (66-100 years) was treated with 5MP2P with very good to excellent clinical results. Two subjects suffered from frequency, severe nocturia, incontinence, constant urgency, and in the third these symptoms were less severe. Clinically, all had enlarged prostates that explained the symptoms. The results were dramatic in the eldest subject within two weeks of therapy. Nocturia of 6-7 trips (every 60-90 minutes) per night was reduced to 1 or 2 nightly (4-5 hours apart). In the other two patients, nocturia 3-4 times (every 2-3 hours) was reduced to once nightly 4-5 hours after retiring. In all cases digital examination of the prostate revealed a detectable reduction in the size of the prostate in 3-4 weeks.
4. Fibrosis of the ventricular myocardium, an outcome of repeated coronary infarcts was treated with 5MP2P in one subject (diagnosed as terminal), with objective evidence of the reduction of the fibrosis (electrocardiogram maps and nuclear resonance determinations). The subject lived for an additional three years, despite the fact that the administration of the drug was terminated after 18 months, due to a limited supply.
5. Inhibition of excessive scar formation by direct application of 5MP2P ointment to skin lesions in 10 cases. Mild to moderate skin laceration or lesions failed to generate skin scars, or caused only minimal scarring when 5MP2P ointment was directly applied to the lesion.

Examples of medical preparations include: (1) capsules, (2) tablets, (3) powders, (4) granules, (5) syrups, (6) injection (intravenous, intramuscular, or drip administration), (7) cream, (8) ointment, (9) inhalation, (10) eye drop, (11) suppositories, (12) pills, etc.

The above preparations are available. Among them, capsules, injections, cream, and ointments are preferred preparations.

TEST EXAMPLE 1

In one capsule, 800 mg, 1200 mg, or 1600 mg of 5MP2P is contained.

TEST EXAMPLE 2

Hydrophilic ointment containing 5 to 10% 5MP2P.

The average oral dosage for anti-fibrotic activity in humans is 3600 milligrams per day, with a range of from about 2400 milligrams to about 4800 milligrams per day. Administration may be in divided dosage - for example, 1200 milligrams three times per day. It is considered to be appropriate in a daily dose of 400 to 2400 mg in total for three administrations per day.

While the invention has been described in detail and with reference to specific embodiments thereof, such have been provided for purposes of illustrating the invention and are not intended as limitations thereon. It will thus be apparent to one skilled in the art that various changes and modifications can be made therein without departing from the spirit and the scope of the present invention.

I claim:

1. A pharmaceutical composition for reparation and prevention of fibrotic lesional tissue in a mammal, comprising 5-methyl-1-phenyl-2-(1H)-pyridone as an active anti-fibrotic ingredient present in an internally administered dosage form in an amount of from about 25 mg per kilogram of body weight per day to about 150 mg per kilogram of body weight per day.

2. A pharmaceutical composition, as defined in claim 1, wherein said 5-methyl-1-phenyl-2-(1H)-pyridone is present in said composition in an amount of from about 100 mg to about 1600 mg.

3. A pharmaceutical composition, as defined in claim 1, wherein said 5-methyl-1-phenyl-2-(1H)-pyridone is present in said pharmaceutical composition in an amount of from about 800 mg to about 1600 mg.

4. A method for the reparation and prevention of fibrotic lesional tissue in a mammal, comprising administering topically to said mammal a pharmaceutical composition containing 5-methyl-1-phenyl-2-(1H)-pyridone as an active anti-fibrotic ingredient in an amount of from about 5% to about 10%.

5. A pharmaceutical composition, as defined in claim 1, wherein said fibrotic lesional tissue is associated with a condition in the group consisting of pulmonary fibrosis, benign prostate hypertrophy, coronary infarcts, cerebral infarcts, myocardiac fibrosis, musculoskeletal fibrosis, post-surgical adhesions, liver cirrhosis, renal fibrotic disease, fibrotic vascular disease, scleroderma, Alzheimer's disease, diabetic retinopathy, and skin lesions.

6. A pharmaceutical composition, as defined in claim 1, wherein said pharmaceutical composition is contained in an article for administration thereof selected from the group consisting of capsules, tablets, powders, granules, syrups, injectable fluids, and pills.

7. A method for the reparation and prevention of fibrotic lesional tissue in a mammal, comprising administering internally to said mammal a pharmaceutical composition containing 5-methyl-1-phenyl-2-(1H)-pyridone as an active anti-fibrotic ingredient, said composition being administered to said mammal at a rate of from about 25 mg per kilogram of body weight per day to about 150 mg per kilogram of body weight per day.

8. A method, as defined in claim 7, wherein said 5-methyl-1-phenyl-2-(1H)-pyridone is administered in an amount of from about 100 mg to about 4800 mg per day.

9. A method, as defined in claim 7, wherein said 5-methyl-1-phenyl-2-(1H)-pyridone is administered in an amount of from about 300 mg to about 4800 mg per day.

10. A method, as defined in claim 7, wherein said 5-methyl-1-phenyl-2-(1H)-pyridone is administered in an amount of from about 100 mg to about 1600 mg contained in a capsule.

11. A method, as defined in claim 4, wherein said fibrotic lesional tissue is associated with a condition in the group consisting of musculoskeletal fibrosis, post-surgical adhesions, scleroderma, glaucoma, and skin lesions.

12. A method, as defined in claim 7, wherein said fibrotic lesional tissue is associated with a condition in the group consisting of pulmonary fibrosis, benign prostate hypertrophy, coronary infarcts, cerebral infarcts, myocardiac fibrosis, musculoskeletal fibrosis, post-surgical adhesions, liver cirrhosis, renal fibrotic disease, fibrotic vascular disease, scleroderma, Alzheimer's disease, diabetic retinopathy, and skin lesions.

13. A method, as defined in claim 7, wherein said pharmaceutical composition is administered by means selected from the groups consisting of capsules, tablets, powders, granules, syrups, injectable fluids, creams, ointments, inhalable fluids, eye drops, suppositories, and pills.

14. A method, as defined in claim 7, wherein said pharmaceutical composition is administered by means selected from the group consisting of creams, ointments, hydrophillic ointments, inhalable fluids, eye drops, and suppositories.

15. A method, as defined in claim 7, wherein said mammal is a human.

16. A pharmaceutical composition for reparation and prevention of fibrotic lesional tissue in a mammal, comprising 5-methyl-1-phenyl-2-(1H)-pyridone as an active anti-fibrotic ingredient present in a topically administered dosage form in an amount of from about 5% to about 10%.

17. A pharmaceutical composition, as defined in claim 16, wherein said fibrotic lesional tissue is associated with a condition in the group consisting of musculoskeletal fibrosis, post-surgical adhesions, scleroderma, glaucoma, and skin lesions.

18. A pharmaceutical composition, as defined in claim 16, wherein said pharmaceutical composition is contained in an article for administration thereof selected from the group consisting of creams, ointments, hydrophillic ointments, inhalable fluids, eye drops, and suppositories.

* * * * *

UNITED STATES PATENT AND TRADEMARK OFFICE
CERTIFICATE OF CORRECTION

PATENT NO. : 5,310,562
DATED : May 10, 1994
INVENTOR(S) : Solomn B. Margolin

It is certified that error appears in the above-indentified patent and that said Letters Patent is hereby corrected as shown below:

Column 9, line 25, insert the following:

TABLE 5
EFFECT OF ORAL 5MP2P UPON CYCLOPHOSPHAMIDE-INDUCED INTERSTITIAL FIBROSIS IN MICE

| NO. MICE | LUNG DRY WT. mgm | LUNG OH-PROLINE microgm/lung | LUNG OH-PROLINE microgm/mgm | LUNG FIBROSIS SCORES## | (N/N) |
|---|---|---|---|---|---|
| GROUP I-A (cyclophosphamide only, 200 mg/kg, i.p.) | | | | | |
| 10 | 50.5+1.3 | 313+10 | 6.01+0.24 | 4.43+0.43 | (0/5) |
| GROUP I-B (cyclophosphamide only, 200 mg/kg, i.p.) | | | | | |
| 8 | 46.8+2.3 | 406+21 | 8.85+0.58 | 3.90+0.23 | (0/5) |
| COMBINED GROUP I-A AND GROUP I-B (cyclophosphamide only, 200 mg/kg, i.p.) | | | | | |
| 18 | 48.9+1.3 | 360+18 | 7.50+0.44 | 4.34+0.26 | (0/10) |

UNITED STATES PATENT AND TRADEMARK OFFICE
CERTIFICATE OF CORRECTION

PATENT NO. : 5,310,562
DATED : May 10, 1994
INVENTOR(S) : Solomn B. Margolin

Page 2 of 3

It is certified that error appears in the above-indentified patent and that said Letters Patent is hereby corrected as shown below:

<u>GROUP II</u> (cyclophosphamide, 200 mg/kg, i.p. PLUS 5MP2P ,500 mg/kg/day, p.o.)

10    52.4+0.9    284+13    5.46+0.31    2.99+0.75  (3/5)#

<u>GROUP III</u> (saline control; <u>NO</u> cyclophosphamide; <u>NO</u> 5MP2P)

6    45.3+1.2    317+20    7.00+0.42    0.26+0.15**(5/5)#

<u>GROUP IV</u>    (5MP2P , 500 mg/kg/day, p.o.; saline; <u>NO</u> cyclophosphamide)

6    39.0+2.8  288+9    7.60+0.60    0.68+0.35**(5/5)#

UNITED STATES PATENT AND TRADEMARK OFFICE
CERTIFICATE OF CORRECTION

PATENT NO. : 5,310,562
DATED : May 10, 1994
INVENTOR(S) : Solomn B. Margolin

It is certified that error appears in the above-indentified patent and that said Letters Patent is hereby corrected as shown below:

Differs significantly (P <0.01) from Combined Group I-A and Group I-B (Student T test for differences between means)

-Differs significantly (P <0.05) from Combined Group I-A and Group I-B (Chi-square two-fold contingency table; incidence of scores 3.0 or less)

Scoring (0 through 6) of lung interstitial hyperplasia and fibrotic nodule formation based on technique recommended by the Pneumoconiosis Committee of the College of American Pathologists, and the National Institute for Occupational Safety and Health (ref: Arch. Path. Lab. Med., vol.106, 1982).

Signed and Sealed this

Ninth Day of January, 1996

Attest:

BRUCE LEHMAN

Attesting Officer

Commissioner of Patents and Trademarks